US009579476B2

(12) United States Patent
Stocking et al.

(10) Patent No.: US 9,579,476 B2
(45) Date of Patent: Feb. 28, 2017

(54) DEVICE FOR INTRODUCING AN AIRWAY TUBE INTO THE TRACHEA

(75) Inventors: John Stocking, Louisville, KY (US); Francis Duque, Louisville, KY (US)

(73) Assignee: Cobra Stylet LLC, Louisville, KY (US)

( * ) Notice: Subject to any disclaimer, the term of this patent is extended or adjusted under 35 U.S.C. 154(b) by 29 days.

(21) Appl. No.: 14/344,115

(22) PCT Filed: Oct. 4, 2011

(86) PCT No.: PCT/US2011/049627
§ 371 (c)(1),
(2), (4) Date: Mar. 11, 2014

(87) PCT Pub. No.: WO2013/052023
PCT Pub. Date: Apr. 11, 2013

(65) Prior Publication Data
US 2015/0258295 A1    Sep. 17, 2015

(51) Int. Cl.
*A61M 16/04* (2006.01)
*A61M 25/01* (2006.01)
*A61B 1/04* (2006.01)
*A61B 1/267* (2006.01)

(52) U.S. Cl.
CPC .......... *A61M 16/0488* (2013.01); *A61B 1/04* (2013.01); *A61B 1/267* (2013.01); *A61M 25/01* (2013.01); *A61M 25/0105* (2013.01); *A61M 2025/0175* (2013.01)

(58) Field of Classification Search
CPC .. A61M 16/00; A61M 16/0488; A61M 16/04; A61M 16/0463; A61M 16/0497; A61M 16/0411; A61M 16/0418; A61M 16/0465; A61M 16/0475; A61M 16/0472; A61M 2025/0004; A61M 2025/0006; A61M 2025/0024; A61M 2025/0175; A61M 2025/018; A61M 2025/0188; A61M 25/002; A61M 25/0029; A61M 25/01; A61M 25/0102; A61M 25/0105; A61M 25/0133; A61M 25/0138
USPC ....................... 128/200.26, 207.14
See application file for complete search history.

(56) References Cited

U.S. PATENT DOCUMENTS

| 4,185,639 A | * | 1/1980 | Linder | A61M 16/0488 128/200.26 |
| 4,607,635 A | | 8/1986 | Heyden | |
| 4,832,691 A | * | 5/1989 | Witzel | A61M 25/104 604/103.07 |

(Continued)

*Primary Examiner* — Justine Yu
*Assistant Examiner* — Colin W Stuart
(74) *Attorney, Agent, or Firm* — John E. Vanderburgh

(57) ABSTRACT

An introducer 40 for guiding an endotracheal tube into a patient's trachea and method for use is provided. The introducer used independently of the endotracheal tube is a malleable elongated tubular body 42 having a proximal end 44 and a distal end 46 and includes an extendible malleable guide member 50 disposed in the bore 48 of the tubular body. Ports 52 are provided in the wall of the tubular body at a point where an operator will normally support the introducer 40 during intubation for contact of the guide member 50 with a finger or fingers of the hand supporting the introducer so that the guide member 50 can be extended without the operator changing the position of the supporting hand while leaving the other hand free for use of a viewing device.

3 Claims, 13 Drawing Sheets

(56) References Cited

U.S. PATENT DOCUMENTS

| | | | |
|---|---|---|---|
| 4,892,095 A | 1/1990 | Nakhgevany | |
| 5,163,941 A | 11/1992 | Garth et al. | |
| 5,257,620 A | 11/1993 | Schermerhorn | |
| 5,309,906 A | 5/1994 | La Bombard | |
| 5,336,182 A | 8/1994 | Lundquist et al. | |
| 5,431,152 A * | 7/1995 | Flam | A61B 1/2676 600/120 |
| 5,498,249 A | 3/1996 | Quinn | |
| 5,558,082 A | 9/1996 | Spencer | |
| 5,733,242 A * | 3/1998 | Rayburn | A61B 1/0052 600/120 |
| 5,749,357 A * | 5/1998 | Linder | A61M 16/0488 128/200.26 |
| 5,803,898 A | 9/1998 | Bashour | |
| 5,919,183 A | 7/1999 | Field | |
| 6,146,402 A | 11/2000 | Munoz | |
| 6,173,199 B1 | 1/2001 | Gabriel | |
| 6,245,029 B1 | 6/2001 | Fujita et al. | |
| 6,432,042 B1 | 8/2002 | Bashour | |
| 6,609,521 B1 | 8/2003 | Belani et al. | |
| 6,672,308 B1 | 1/2004 | Gaspari | |
| 6,718,970 B2 | 4/2004 | Sniadach | |
| 6,874,504 B1 | 4/2005 | Raspallo | |
| 6,877,512 B2 | 4/2005 | Imai et al. | |
| 6,929,600 B2 | 8/2005 | Hill | |
| 7,127,758 B2 | 10/2006 | Gabbay | |
| 7,174,894 B1 | 2/2007 | Raspallo | |
| 7,243,653 B2 | 7/2007 | Nelson | |
| 7,322,357 B2 | 1/2008 | Nelson | |
| 2007/0175482 A1 | 8/2007 | Kimmel et al. | |
| 2008/0017195 A1 | 1/2008 | Yoshida | |
| 2008/0230056 A1 * | 9/2008 | Boedeker | A61B 1/267 128/200.26 |
| 2010/0012130 A1 * | 1/2010 | Guerra | A61M 16/0465 128/207.15 |
| 2010/0307489 A1 * | 12/2010 | Harms | A61M 16/0488 128/200.26 |

* cited by examiner

DEVICE FOR INTRODUCING AN AIRWAY TUBE INTO THE TRACHEA

FIELD OF THE INVENTION

This invention relates to apparatus for the introduction of an airway tube into a patients trachea and more particularly to an introducer for guiding the airway tube into the trachea.

BACKGROUND OF THE INVENTION

Endotracheal tubes (ETT) are inserted into a patient's trachea to aid breathing during medical emergencies and in combination with a laryngeal mask are employed during surgical procedures to provide ventilation and to administer anesthesia. It is essential that intubation of the patient be accomplished in as short a time as possible both in a medical emergency and especially during surgery where there is a period where the patient is not breathing due to administration of muscle relaxant.

An ETT 10 is shown in FIG. 1. An ETT comprises a tubular shaft 12 with a distal end 14, a proximal end 15, an inflatable cuff 16 and an inflation lumen 17. During intubation the distal end 14 of the ETT is inserted into a person's mouth and slidably positioned into the person's trachea such that proximal end 15 projects outward from person's mouth. Inflatable cuff 16 is then used to secure the ETT 10 in the trachea. Inflatable cuff 16 is inflated by supplying air at inflation lumen 17. Oxygen and/or anesthetics are then supplied to the person by supplying them utilizing proximal end 15 of ETT.

In order to successfully intubate a patient it is essential that the tube be guided to and through the glottis. Traditionally this is accomplished visually by the operator but in many cases insertion into the glottis difficult to accomplish such as if the operators view is obscured because the patient is improperly positioned or because of anatomic abnormalities or obesity. Various devices such as introducers (introducers) or stylets have been designed as an aid to intubation.

A stylet is a stiff but malleable elongated member inserted into the bore of the ETT to maintain rigidity and to allow the ETT to be shaped so as to aid in the insertion of the ETT into the patients trachea. FIG. 2 is a drawing of a standard stylet 20 and ETT 10 assembly 21 inserted into the trachea 22 of a patient. The ETT 10 is pre-loaded over the stylet 20 before intubation. A distal end 24 of standard stylet 20 is inserted into the ETT 10 while its proximal end 26 extends outward from the proximal end 15 of the ETT 10. Once the assembly is inserted the operator withdraws the stylet 20 through the proximal end of the ETT. Maneuvering of the assembly 21 during the procedure must be done at proximal end 15 of the ETT and proximal end 26 of the stylet 20. This normally requires the operator to change hand positions during a critical stage of the intubation or an assistant since one of the operator's hands are required to support the assembly 21 while the other either holds a laryngoscope or maneuvers the assembly from the proximal ends 15 and 26.

The standard stylet 10, together with the ETT 12 can be bent to form a shape that facilitates insertion into the trachea of a person. Stylets are often made of malleable metals such as stainless steel or copper. They are intentionally designed to withstand much deformation force. Unfortunately this makes the airway vulnerable to injury if the stylets are advanced without being surrounded by an ETT. Keeping the distal tip of the stylet within the ETT and not allowing the tip to extend beyond the ETT's distal tip minimizes the risk of airway trauma from the unyielding stylet. These stylets often even have adapters to hold the ETT in place and prevent the stylet from sliding forward relative to the ETT. Unfortunately, styletted ETTs aren't as maneuverable as thin introducers. When they are covered by an ETT, the ETT can also obscure the view of the airway and glottis from a proximal direction as when using traditional laryngoscopes and newer videoscopes.

As illustrated in FIG. 3 a conventional Eschmann-type introducer 28 is a thin elongated member defining a proximal end 30 and a distal end 32 and that is inserted into the patient's trachea, normally using a laryngoscope (not shown). After the distal end 32 of the introducer 28 has been inserted, the laryngoscope is removed and the ETT is railroaded (advanced) over the introducer 28 from the proximal end 30 and guided by the introducer into the trachea.

The Eschmann-type tracheal tube introducer (formerly known as the gum elastic bougie) is a 60 cm long, 15 French Gauge, flexible device with a coude' distal tip. During use a curve is also formed towards its distal end. The tracheal tube introducer is used to facilitate difficult intubation. It should not be confused with the more rigid stylet 20 discussed above, which is inserted into the endotracheal tube and used to alter its shape prior to intubation. Unlike the stylet 20 the introducer 28 is inserted independently of the ETT and is used as a guide. Since the introducer is considerably softer, more flexible, and blunter than a stylet, use of an introducer is considered to be a relatively atraumatic procedure compared to a procedure using only a stylet.

FIG. 4 illustrates an intubation in which the introducer 28 has been introduced into the trachea 34 of a patient following which the ETT 30 has been advanced down the introducer and guided thereby into the trachea. After intubation the introducer 28 may be removed or may remain in place if it contains a bore through which fluids may be introduced.

Light guided devices employing transillumination such as ETT stylets, Light wands [e.g., Trachlight™ (Laerdal), Vital Light™ (Vital Signs), Trachlite™ (Rusch), Surch-Lite™ (Aaron Medical Industries, Inc.)] have been used to indirectly indicate entrance into the trachea. These devices also require that the ETT be preloaded and thus do not allow the ETT to be railroaded after tracheal placement of the light wand is confirmed.

To further aid intubation flexible fiber optic bronchoscopes and videoscopes may be provided with an optical function. These devices employ a scope through which the operator can directly view the distal end of the device. These aids are often inadequate in reliably assisting placement of ETTs. A significant challenge when using videoscopes has been guiding the ETT into the trachea. Even though there has been a vast improvement in visualizing the glottis with videoscopes, there have been difficulties noted in guiding the ETT to and through the glottis. For example, with stylet style videoscopes the field of view may be obscured by the large diameter of the ETT. Also since the stylet style videoscope is surrounded by the ETT some maneuvering is impossible. An additional problem with devices containing optics is that bending of the device in certain regions, especially at the distal tip cannot be accomplished because this is where the optical component is located.

In an attempt to overcome some of the deficiencies of stylet style videoscope devices the stylet can be provided with an extendible member telescopingly disposed within the body of the stylet. For example Patent Application Publication 2008/0017195 describes an extendable lighted stylet that is inserted into the bore of an ETT. The stylet contains an extendable member that carries a light source which can be extended using a handle portion at its proximal end. The field of view can be obscured by the larger diameter ETT and operation of the stylet requires the operator to use one hand at the proximal end while supporting the tube and stylet with the other hand. This is difficult if a laryngoscope is also being utilized and in fact may require two people to successfully perform the intubation. In addition bending the device to aid intubation can be hampered by the optical components.

A similar system is described by Rayburn et al. in U.S. Pat. No. 5,733,242. A stylet with a scope tube contains a light transmitting optic fiber. The stylet is disposed in the bore of an ETT. The scope tube can be used to guide an ETT. This device is subject to the same problems described above, especially as operation must be accomplished at the proximal end handle portion.

Rigid stylets have also been used in combination with conventional laryngoscopes for intubations to provide an enhanced view of the glottis during the procedure. However it has been well documented that providing a good view of the glottis does not always correlate with successful airway intubation. The limitations of video laryngoscopes in advancing the ETT through the vocal cords and into the glottis have been well described.[1,2] Using a stylet to curve the ETT through the vocal cords and into the trachea has often proven difficult due to, among other things, having the bevel of the ETT become stuck at the arytenoids, or impact the anterior wall of the larynx. In addition the discomfort to the patient may be increased. The use of a softer stylet has been suggested to allow for the adjustment of the ETT and result in faster intubation times.[3]

[1] Doyle D J, Zura A, Ramachandran M, *Videolayngoscopy in the management of the difficult airway* (Letter). Can J Anesth 2004; 51:95
[2] Cooper R M, *Videolarynoscopy in the management of the difficult airway* (Letter, reply) Can J Anesth 2004; 51: 95-6
[3] Rai M R, Deering A, Verglose C, *The Glidescope system: a clinical assessment of performance*. Anesth 2005; 60:60-4

Stylets require that the ETT be loaded over the stylet. A problem with the preloaded-ETT-over-the-stylet designs is that they often require use of a control mechanism located at the proximal end. This can be far behind the operator's supporting hand. The operator's other hand must continue to hold the videoscope in a fixed position, so maneuvering from the proximal end of the ETT requires distracting maneuvers by the operator or the help of additional personnel trained in the use of the device. Also, the larger diameter ETT can interfere with operator's line of sight during intubation.

The Eschmann-type introducer has been successfully used for numerous difficult intubations in combination with traditional laryngoscopes. The introducer permits one hand operation from a medial portion of the device making it easier to maneuver the distal end during difficult intubations. Some difficulties have been noted when the introducer is used in combination with the more recently developed videoscopes. Unfortunately, intubating-introducers such as the Eschmann introducer weren't originally conceived of for use with videoscopes. Videoscopes have created the need for more dynamically shapeable designs to adjust to the unique angles of approach required when viewing the glottis through the videoscope. For example, a good view can often be obtained and an introducer can be advanced close to the glottis, but there may be difficulty advancing the tip of the introducer through the glottis. Often the tip of the introducer can be seen with the glottis clearly in the background, but the distal tip of the introducer can't be advanced through the glottis. This often occurs because the introducer must be pre-bent to align with the glottis but can't be extended distally in the direction toward which the distal tip points In an effort to alleviate this problem some manufacturers have inserted a flexible wire into the introducer to provide for improved molding of the introducer so that the distal end portion can point towards the glottis. But there is no provision for advancing the distal tip toward and through the glottis. Even with the proximal portion of a telescoping device pointing in the general direction of the glottis, maneuvering is still needed to actually advance the distal portion through the glottis.

Yoshida et al. (US Patent Application Publication US2008/0017195, Jan. 24, 2008) teaches a stylet that includes an extendable member carrying a light at its distal tip. This device is subject to many of the disadvantages described above and in addition includes a handle portion at the proximal end that requires the ETT be preloaded over the stylet. Manipulation is by the handle portion at the proximal end and cannot be maneuvered using one hand.

It would be desirable to have an introducer that does not require preloading of the ETT and that does not obscure the view through a videoscope. In addition it would be desirable to have an introducer readily moldable into a desired shape and that has a maneuverable extendable member that can be readily inserted into the trachea using one hand and that can be supported and controlled at a point medial the distal and proximal ends of the introducer.

OBJECTS OF THE INVENTION

Accordingly, it is an object of our invention to provide an introducer for an ETT that doesn't obscure the view through a videoscope and that has the flexibility, maneuverability and softness of an Eschmann-type introducer.

It is a further object to provide an introducer having a telescoping retractable/extendible guide disposed in the introducer at its distal end that can be maneuvered into the patient's trachea for guiding the ETT.

Yet another object is to provide an introducer that can be supported by one hand at its medial portion and operated to extend and retract the telescoping retractable/extendible guide without changing the placement of the supporting hand.

Another object is to provide an introducer in which the telescoping retractable/extendible guide can be dynamically shaped and reshaped as needed.

Another object is to provide an introducer having a flexible proximal end portion that can be shaped for alignment with the line of sight of a videoscope.

Another object is to provide an introducer for an ETT that does not require preloading of the ETT and that can be placed independently of and prior to the insertion of an ETT.

These and other objects and advantages of the invention will become apparent from the following description of the invention taken in conjunction with the drawings in which like reference numbers refer to like parts.

SUMMARY OF THE INVENTION

As used herein the terms "introducer", "bougie" and "Eschmann-type introducer" are used interchangeably to mean a lightweight, elongated body that is seemingly equally-balanced proximally and distally when when held in its mid-region by the operator. It is designed for use independently of an ETT and once in the trachea the ETT is advanced over the introducer and guided thereby into the trachea. The introducer is then removed from the bore of the ETT. This is to be contrasted with "stylet" which is used to denote an elongated body that is loaded into the ETT prior to intubation and which is designed to shape the ETT for intubation. Stylets, which are able to withstand deformation force, can injure the patient if improperly maneuvered during intubation. With most stylet applications the distal tip remains in the distal portion of the ETT to avoid injury to the patient.

In accordance with the invention there is provided a flexible introducer for an ETT comprising an elongated body defining a proximal end and a distal end. It preferably is of sufficient length so its distal tip can be placed in a patient's trachea while its proximal end extends from the mouth of a patient the length an ETT. A bore extends from the proximal end of the body to open at the distal end. A flexible elongated guide member is telescopingly disposed in the bore for rotation, extension and retraction of the member with respect to the distal end of the elongated body. At least one port is provided in the wall of the elongated body medially of the proximal and distal ends, preferably at the area of the body normally supported by the operator during intubation, for communication between the exterior of the body and the guide to permit the operator to maneuver the telescoping guide with the finger or fingers of the hand that is supporting the introducer. The distal end portion of the flexible introducer is curved with respect to the longitudinal axis of the proximal body portion and the flexible telescoping guide takes the curve of the distal end portion of the introducer. The telescoping guide may be provided with a through running bore for fluid delivery to a patient.

In one embodiment one end of the telescoping guide extends from the proximal end of the introducer and a cap having a diameter greater than outside dimension of the introducer is formed on the extending end of the telescoping guide for contact with the proximal end of the introducer to prevent over extension of the telescoping guide from the distal end of the introducer.

In another embodiment the bore of the introducer is larger at the proximal end portion of the introducer and opens medially of the proximal and distal ends to a smaller bore extending from the distal end of the introducer to form an annular shoulder medially located in the introducer that defines a stop for a cap formed on the proximal tip of the guide member that is received in the larger proximal bore.

In another embodiment the proximal end of the introducer and bore are constricted and as the proximal end of the telescoping guide is inserted into the bore through the distal end of the introducer the proximal end of the telescoping guide contacts the restriction in the bore of the introducer. Insertion is continued to cause the guide to bow outwardly through the port formed in the sidewall of the introducer. The bowed portion provides a convenient means for advancing the telescoping guide by the operator's finger or fingers.

In another embodiment the introducer is formed in two sections, a proximal section and a distal section that can be extended relative to the proximal section. In this embodiment rather than a telescoping guide member extending from the bore of the introducer the distal section of the introducer itself can be extended and maneuvered into the patient's trachea. The ETT can then be railroaded along the proximal section and guided by the extended distal section into the trachea. In its fully retracted position the introducer operates as a conventional introducer.

Other features, objects and advantages will become apparent from the following description of the invention taken in conjunction with the drawings where like reference numbers denote like parts.

DESCRIPTION OF THE INVENTION

Figure 1:
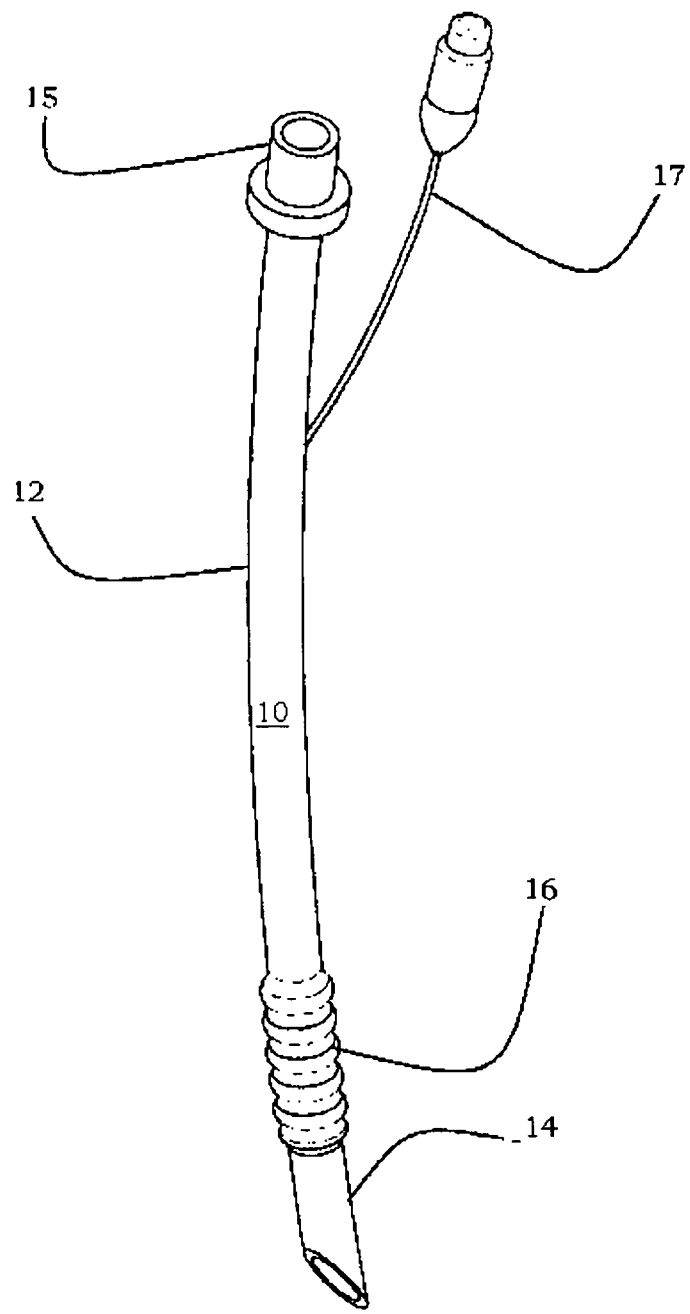
FIG. 1 is perspective view of a conventional ETT.
Figure 2:
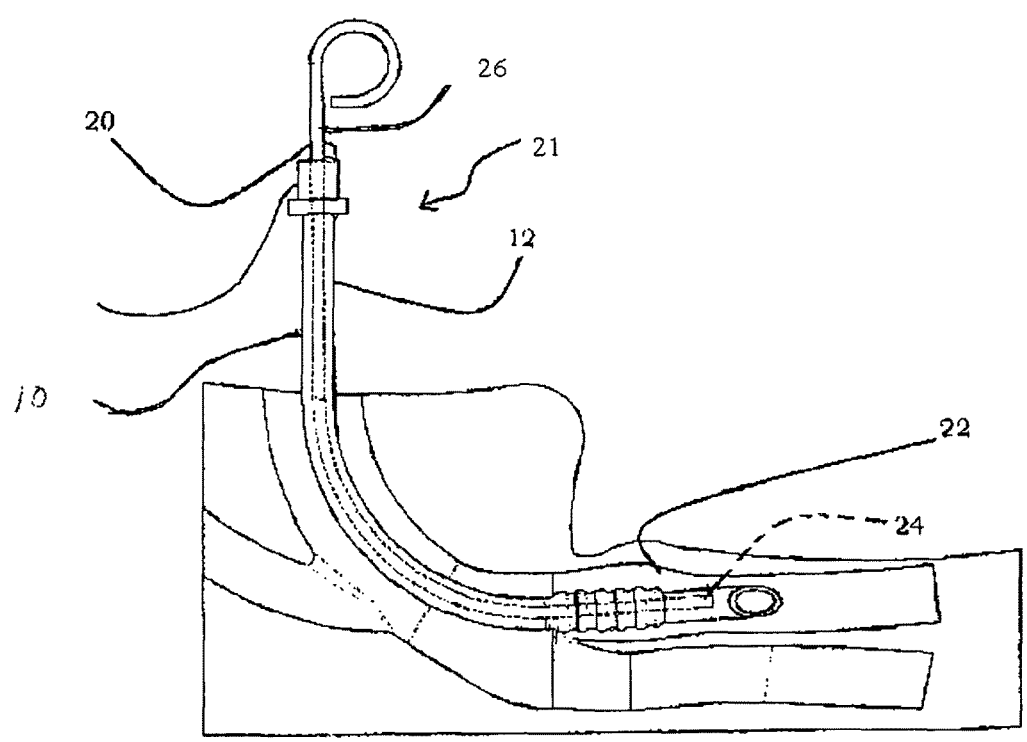
FIG. 2 is a view of a conventional stylet inserted in an ETT and inserted into the trachea of a patient.
Figure 3:
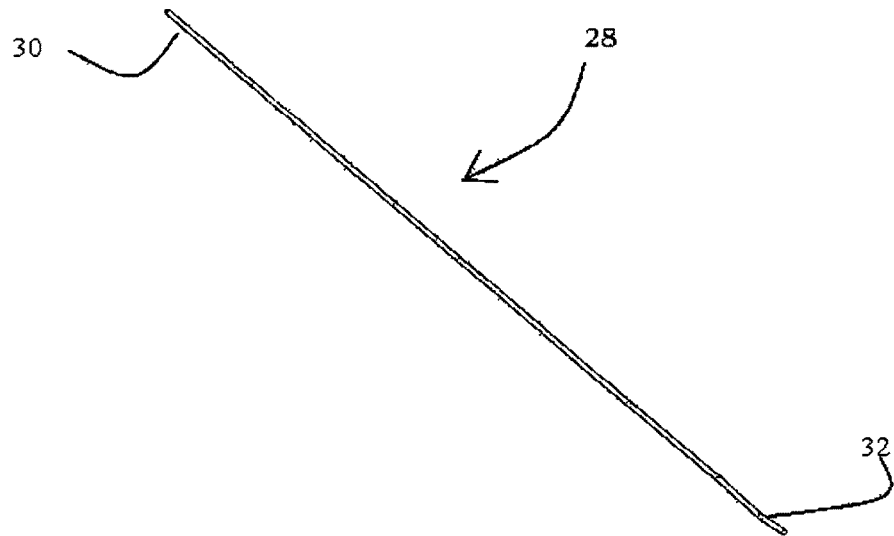
FIG. 3 illustrates a conventional Eschmann-type introducer.
Figure 4:
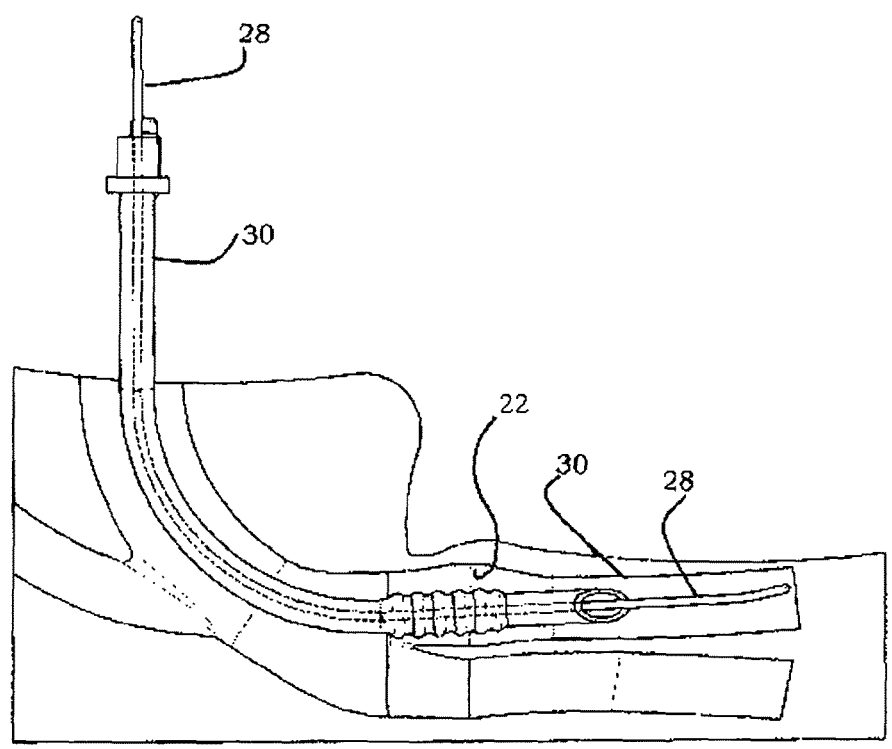
FIG. 4 illustrates an intubation using a conventional Eschmann-type introducer and conventional ETT.
Figure 5:
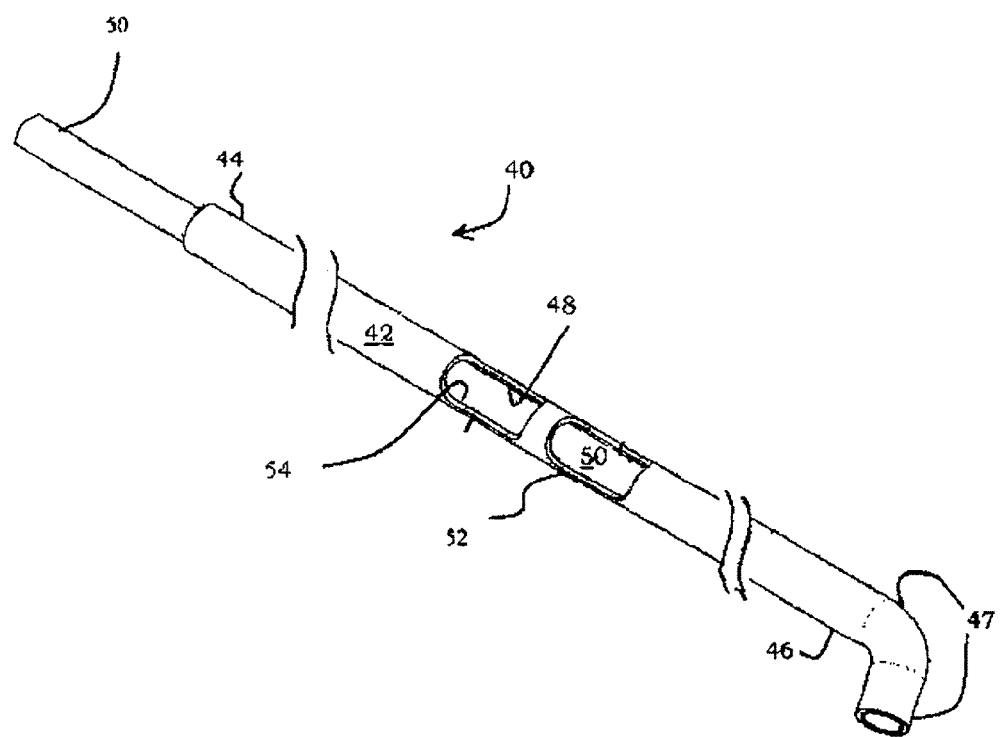
FIG. 5 illustrates an introducer in accordance with the invention broken away for compactness of illustration with a telescoping guide member fully retracted in the tubular body.
Figure 6:
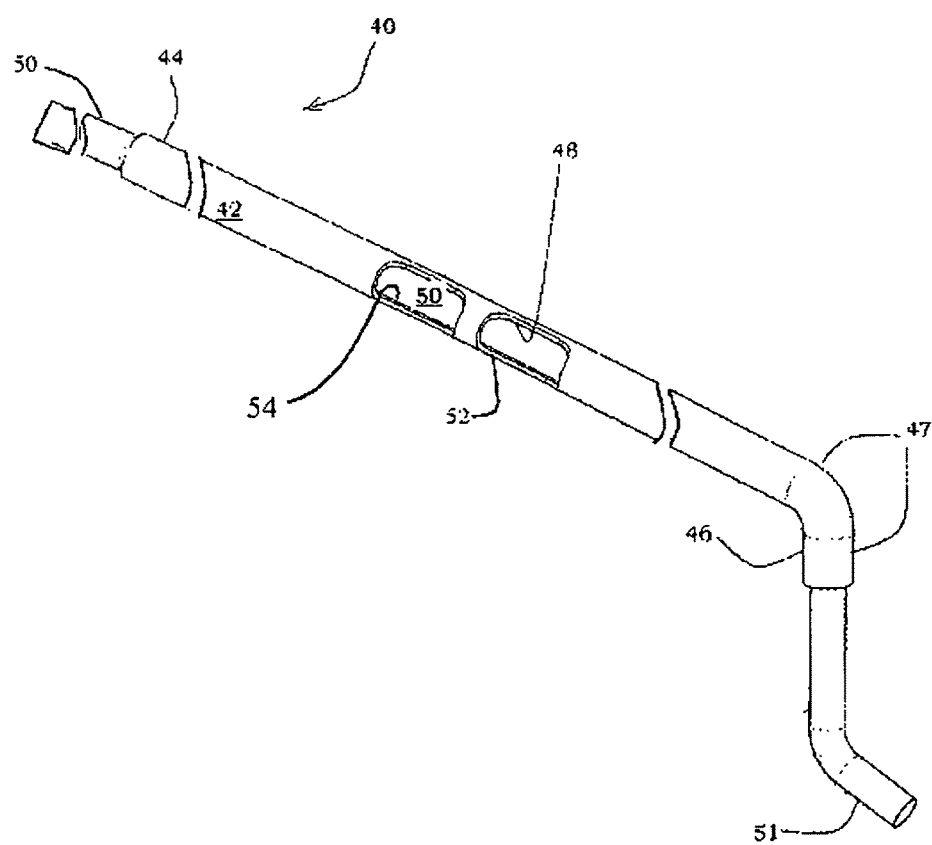
FIG. 6 illustrates the introducer of FIG. 5 with the telescoping guide member extended from the distal end to the tubular body.
Figure 7:
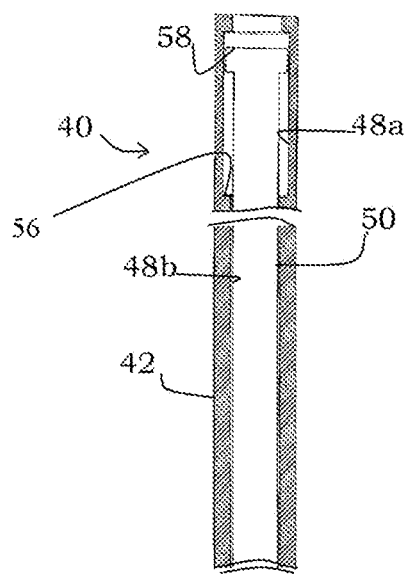
FIG. 7 is a sectional view, partially broken away for compactness of illustration, of the introducer of FIG. 5 illustrating one embodiment of a stop to prevent over extension of the telescoping guide member.

Referring to FIGS. 5, 6, and 7 an introducer in accordance with the invention is shown generally as 40. The introducer 40 comprises an elongated tubular body 42 defining a proximal end 44 and a distal end 46. A through-running bore 48 opens at the proximal and distal ends, 44 and 46 respectively, of the tubular body 42. A portion 47 at the distal end 46 is curved to into a J shape (Coude' Tip). The proximal portion of the tubular body 42 may be straight or may define a curve or an arc. The shape of the proximal and distal portions of the body 42 is a matter of choice depending on the operator's preference and the physiology of the patient. In this regard the body is often shaped just prior to intubation. The length of the tubular body 42 will normally range from about 500 mm to about 700 mm although other lengths can be used with good results. The outside diameter of the body 42 is less than the inside diameter of an ETT, which for humans ranges from 2 mm to 15 mm, so that the ETT can be advanced along the body without interference. The size of the ETT is chosen based on the patient's body size with the smaller sizes being used for pediatric and neonatal patients and accordingly the size of the tubular body 42 will depend on the size of the ETT.

Disposed in the bore 48 of the tubular body 42 is a flexible telescoping guide member 50 having an outside diameter smaller than the inside diameter of the bore 48. The telescoping guide member 50 can move longitudinally within the bore 48 between a guiding position with a distal end portion 51 of the telescoping guide member extending out of the distal end 46 of the tubular body 42 (FIG. 6) and a retracted position with its distal portion within the bore (FIG. 5). The telescoping guide member 50 is of least sufficient length so that in the retracted position its distal end terminates within the distal end 46 of the introducer 40 and its opposite end terminates at the proximal end 44 of the introducer or, as shown, extends from the proximal end. In addition in its retracted position, the distal portion 51 of the flexible guide member 50 assumes the J-shape of the curve of the distal portion 47 and retains the shape in the guiding position. The guide member 50 can be rotated as necessary to maneuver the distal portion 51 into the trachea or to maintain visual contact through the videoscope or laryngoscope.

Figure 8:
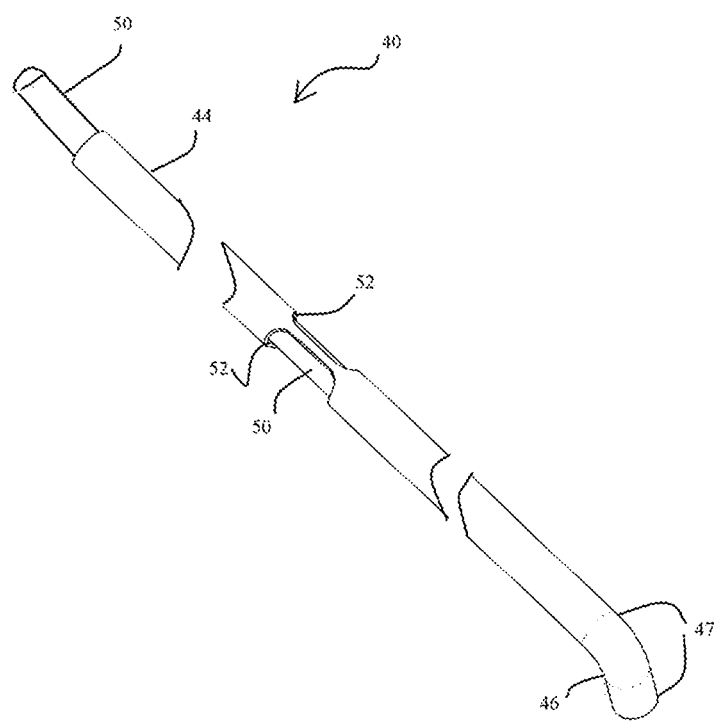
FIG. 8 is a view of the introducer of FIG. 5 cut away for compactness of illustration showing opposed control ports in the sidewall of the tubular body.

One or more control ports 52 in the wall of the tubular body 42 are provided medially the proximal end 44 and the distal end 46 of the tubular body 42. Ports 52 and 54 are of sufficient size to allow the operator's finger or fingers to contact the guide member 50 for extension, retraction and rotation. Preferably ports 52 and 54 are medially located on the tubular body 42 at the location that the operator holds the introducer during the intubation procedure so the operator can support the introducer 40 and maneuver the guide member 50 with the same hand. This leaves the other hand free to use a viewing device such as a videoscope or laryngoscope while maneuvering the tubular body 42 and the guide member 50 when extended. The control ports 52 and 54 may be arranged as shown in FIGS. 5 and 6 for single finger control or be on opposed sides of the tubular body as illustrated in FIG. 8 for control using several fingers, for example the thumb and index finger.

Over extension of the guide member 50 is undesirable and could produce complications if extended too far into the patient's airway. One embodiment to prevent over extension of the guide member 50 is illustrated in FIG. 7. In this embodiment a portion of the bore 48*a* at the proximal end portion 44*a* of the tubular body 42 is enlarged with respect to the distally extending portion 48*b* to define an annular shoulder 56 at the junction of the two portions. The proximal end of the guide member 50 is disposed in the proximal portion 48*a* of the bore 48 and is enlarged to define a cap 58 having a diameter larger than the portion 48*b* of the bore 48. Axial movement of the guide member 50 is limited by contact between the under surface of the cap 58 and the annular shoulder 56 to prevent over extension of the guide member. Preferably the annular shoulder 56 is located in the bore 48 to limit extension of guide member 50 from the distal end 46 of the tubular body 42 to about 20 mm.

The introducer 40 is light weight and is relatively soft having a hardness in the range of 40 to 70 Shore A. Materials that exhibit the desired hardness, rigidity and flexibility include polyvinyl chloride, polyurethane, polyethylene, fluorinated hydrocarbon polymers, silicone rubber materials, polyamides, flexible nylon and flexible silicone materials. Preferably the material of construction is sufficiently flexible to be formed into a shape, such as a bent distal tip, and return to that shape upon release of external force applied when the guide member 50 is retracted into the tubular body 52.

Figure 9:
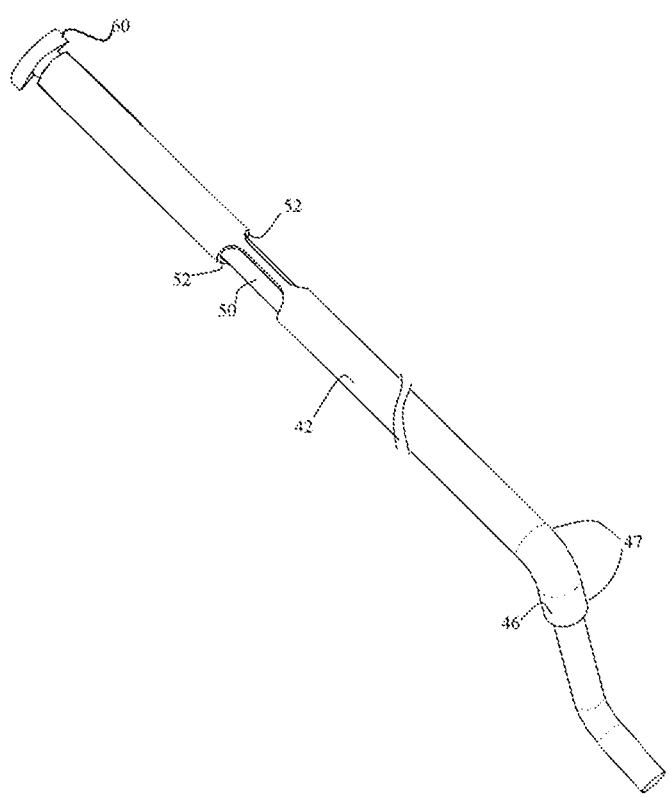
FIG. 9 illustrates another embodiment of a stop to prevent over extension of the guide member.

Another embodiment is illustrated in FIG. 9 in which a proximal portion 57 of the guide member 50 extends from the proximal end 44 of the tubular body 42. A cap 60 having a diameter equal to or greater than the outside diameter of the tubular body 42 is formed on the extending end of the guide member 50. Axial travel of the guide member 50 distally during extension is limited by contact between the cap 60 and the proximal end 44 of the tubular body 42. The length of the extending proximal portion 57 is equal to the desired maximum extension of the distal end of the guide member 50.

Normally the telescoping guide member 50 will initially be fully retracted. The operator will normally support the introducer 40 with one hand at a medial part of the tubular body 42. With the other hand the videoscope or laryngoscope is introduced and activated for viewing the progress of the intubation. Absent any complications the introducer 40 is inserted in a conventional manner through the glottis and into the trachea. However, in the event there is a problem inserting the introducer 40 into the trachea, such as where the patient's head cannot be correctly positioned or due to anatomic abnormalities or with pediatric patients, the operator can extend the guide member 50 using the fingers of the supporting hand and maneuver it by extension and, if necessary, rotation of the guide member through the glottis and into the trachea. The guide member 50, having a smaller diameter than the introducer 40, is more readily inserted through the glottis. Following this the ETT is placed over the introducer 40 and is guided over the introducer and the extended guide member 50 through the glottis and into the trachea.

The entire intubation procedure is accomplished using one hand leaving the other hand free to operate a videoscope or laryngoscope. The fingers of the supporting hand of the operator also can control the extension of the guide 50 and can rotate the guide so that the J-shaped distal portion 51 can be better positioned to enter the glottis and trachea of the patient without the necessity of changing hand position to use awkward control mechanisms. Intubation is faster since it is unnecessary for the operator to reposition his hand in order to maneuver the guide member 50 and since the ETT is positioned on the introducer 40 after it and/or the guide member 50 has entered the trachea it does not interfere with the view from a videoscope.

Figure 10:
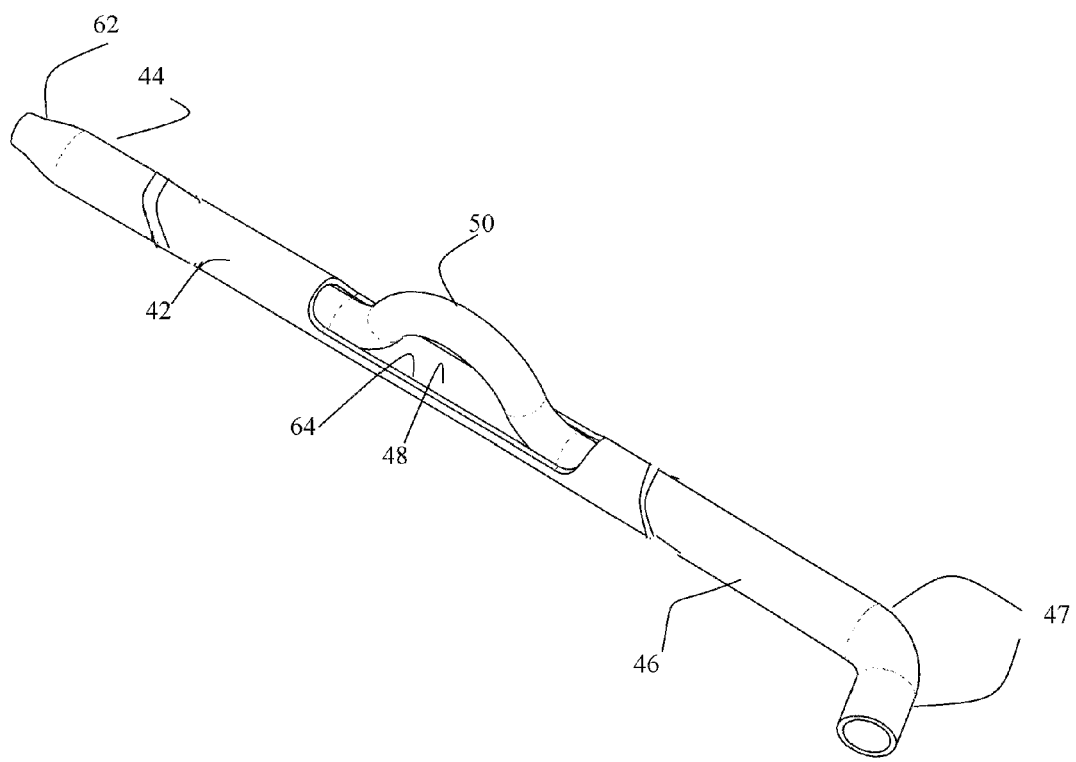
FIG. 10 is a perspective view of an embodiment of the introducer of the invention with a medial portion of the telescoping guide member outside of the introducer body for grasping the guide with fingers of the operator's supporting hand to maneuver the telescoping guide member with the supporting hand.

Referring to FIG. 10 wherein like reference numbers refer to like parts, an alternative finger control is illustrated that is particularly suited for maneuvering the telescoping guide member 50 with a single finger. In this embodiment the proximal end 44 of the tubular body 42 is crimped or constricted at 62 to prevent the guide member from extending beyond the proximal end. An elongated opening 64 is formed in the side wall of the tubular body 42 medially of the proximal end 44 and the distal end 46. The opening 64 is preferably located along the tubular body 42 at the operator's normal support position of the introducer 40 during intubation. The guide member 50 is loaded into the bore of the tubular body 42 from the distal end 46 and is moved axially through the bore to contact the constriction 62 which prevents the end of the guide member from moving out of the proximal end 44. Continued application of axial force on the guide member 50 at the distal end 46 forces the part of the guide member at the elongated opening 64 to project through the elongated opening in the form of an arch through which the operator's finger can manipulate the axial movement of the guide member 50. It will be understood that the embodiment of the invention illustrated in FIG. 7 and discussed above can be utilized equally well in this embodiment. Intubation of a patient using this embodiment of the invention is the same as described above.

Figure 11:
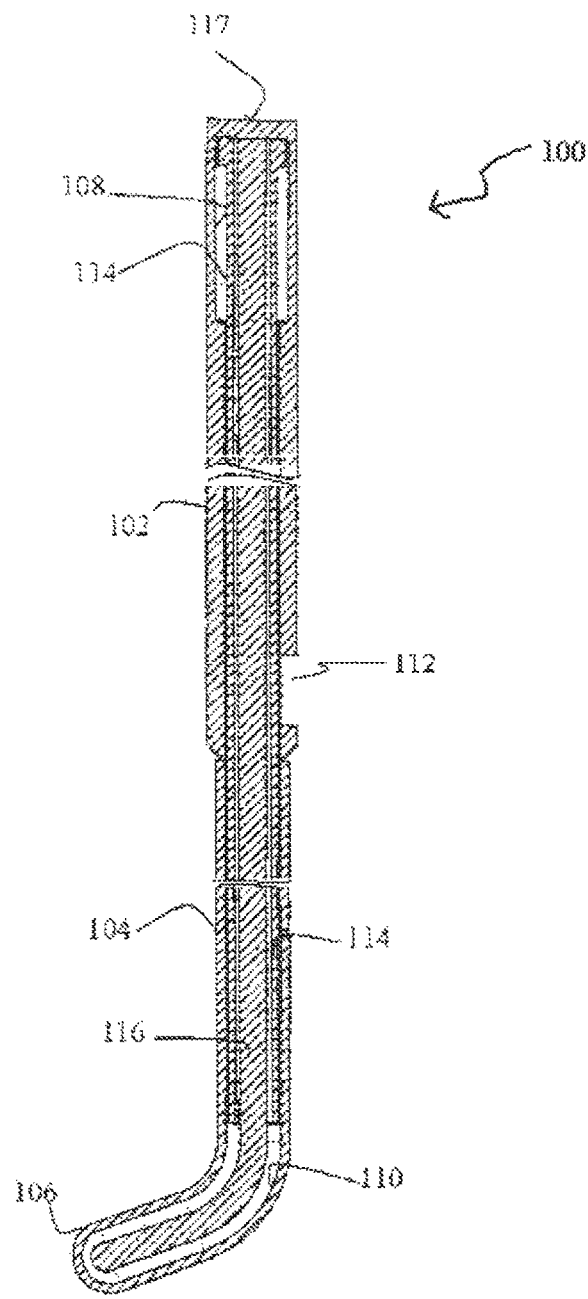
FIG. 11 is a sectional view of another embodiment of an introducer in accordance with the invention comprising a proximal section and an external, extendable distal section showing the distal section fully retracted.
Figure 12:
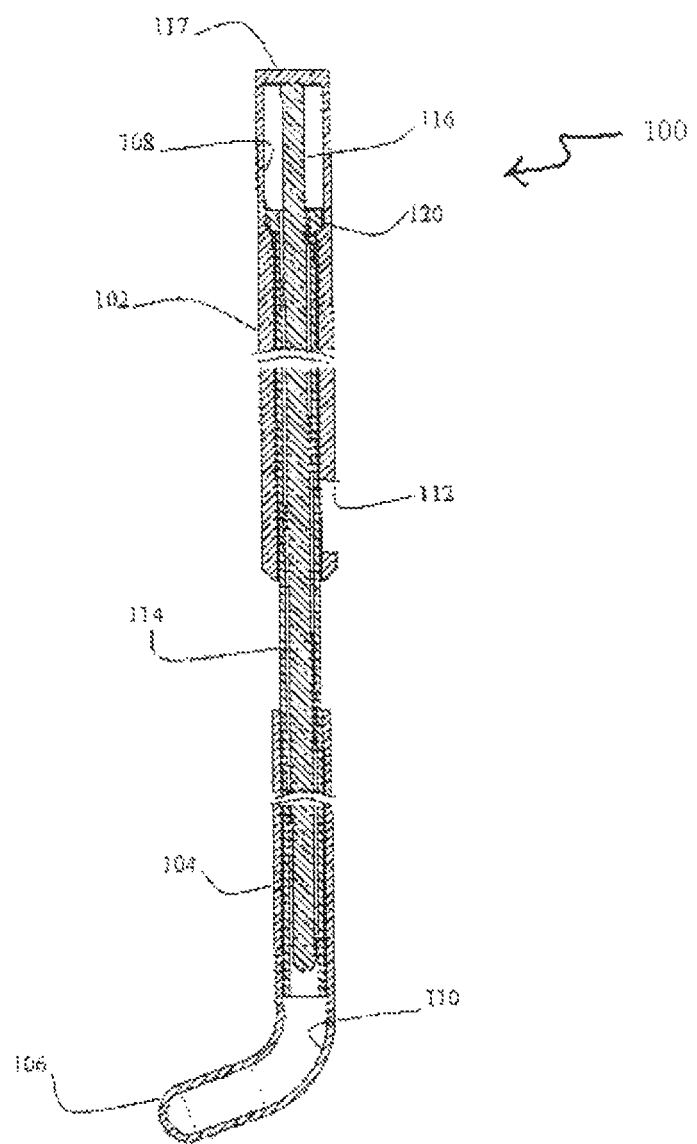
FIG. 12 is a sectional view of an introducer in accordance with the invention comprising a proximal section and an external, axially extendable distal section showing the distal section in an extended position.

The invention thus far has been described in connection with an introducer that contains a flexible, telescoping guide member that can be controllably extended, retracted and maneuvered without changing hand position to guide an ETT for intubation and which is suited for use with a videoscope or laryngoscope. In another embodiment illustrated in FIGS. 11, 12, 13 and 14 the distal portion of the introducer itself extends and retracts rather than containing a telescoping guide member. With this embodiment the operator can perform intubation much as would be performed using an Eschmann type introducer the use of which the operator may be more familiar and may prefer. FIGS. 11 and 12 are sectional views of an introducer 100 in accordance with the invention comprising a tubular proximal section 102 and a flexible guide member assembly comprising a tubular distal section 104, separate from the proximal section, which terminates in a distal tip that is angled with respect to the axis of the proximal section. The distal section 104 is axially movable with respect to the proximal section 102 between a retracted position (FIG. 11) and an extended position (FIG. 12). The bore 108 of the proximal section 102 is through-running while the bore 110 of the distal section 104 is closed at the distal tip 106. Proximal port 112 located along the proximal section 102 to be positioned at the point where an operator normally places one hand to support and maneuver the introducer during intubation. The finger or several fingers of the hand supporting and maneuvering the introducer 100 can be used to extend the distal section 104 through the proximal port. A convenient location for the proximal port 112 is on the proximal section 102 adjacent the abutting end of the distal section 104 when it is in the retracted position which preferably is approximately at the balance point of the introducer 100 where it is normally supported by a hand of the operator.

A tubular cylinder 114 extends through the bore 108 and into the bore 110 and is slidingly disposed in bore 108 and secured in the distal section 104 for axial reciprocation of the distal section with respect to the proximal section 102 to extend and retract the distal section. The tubular cylinder can be secured in the distal section 104 by a suitable adhesive or be integrally formed as part of the distal section. A support core 116 extends through the bore 108 of the proximal section 102 and the bore of the tubular cylinder 114 into the distal section 104, such as into the bore 110 as illustrated. The proximal end of the core 116 is secured in a cap 117 that closes the end of the proximal section 102. In the embodiment illustrated the distal section 104 moves axially along the core.

Figure 13:
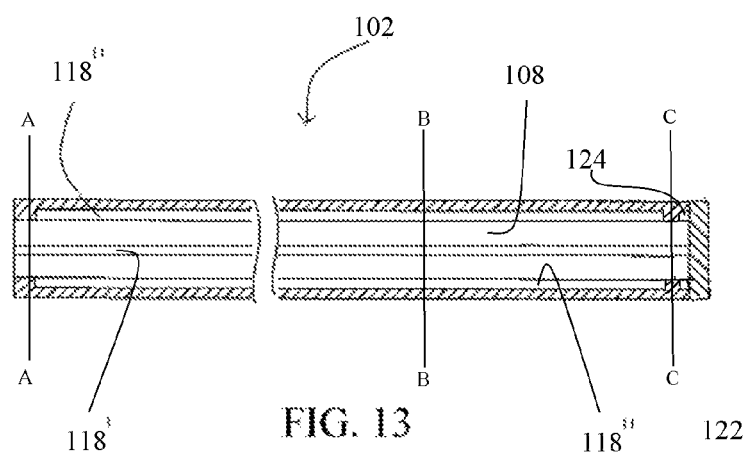
FIG. 13 is a top sectional view of the proximal section of FIG. 11 without the apparatus for extending and retracting the distal section.
Figure 14:
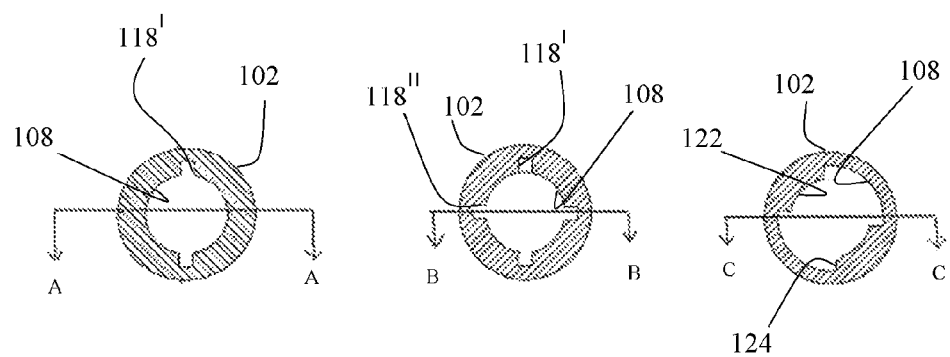
FIG. 14 illustrates end sectional views of the proximal section of FIG. 11 and FIG. 13.

It will be understood that the bore 108 of the proximal section 102 and the proximal end of the tubular cylinder is adapted to prevent the tubular cylinder 114 from leaving the bore 108 resulting in the unintentional disassembly of the introducer 100 during use. In addition, rotation of the distal section 104 is highly undesirable and will essentially prevent maneuvering of the introducer 100, for example to maintain visual contact. Referring to FIGS. 13 and 14, four channels 118 opening to the bore 108 are formed in the wall of the proximal section 102 and are arranged about the bore in opposed pairs, for example at 6 and 12 o'clock (118') and 3 and 9 o'clock (118"). Corresponding lugs 120 (FIGS. 11 and 12) are provided on the proximal end of the tubular cylinder 114 and are received in the channels One pair of the channels 118' open to mouth of the bore 108 while the other pair of channels 118" terminate at the distal end of the proximal section 102. As illustrated in FIGS. 13 and 14 the channels 118" at 3 and 9 o'clock terminate at the distal end of the proximal section 102 to prevent over extension of the distal section 104 by contact between the corresponding lugs 120 and the terminal wall of the channels 118". The channels 118' oriented at 12 and 6 o'clock open at the mouth of the bore 108 for assembly and disassembly of the introducer 100 when the tubular cylinder 102 is rotated so that the corresponding lugs 120 are received in the channels 118'. The bore 108 at the proximal end of proximal section 102 is provided with opposed thickened wall sections 122 which cooperate with the adjacent wall of the bore to define stop surfaces 124 to restrict rotation of the tubular cylinder 114 by acting against the lugs 120. As illustrated, the stop surfaces are aligned with the channels 118 so that, when the distal section 104 is fully retracted the tubular cylinder 114 can only be rotated counter clockwise to align the lugs 120 with channels 118' or clockwise to align the lugs with the channels 118".

The body of the distal section 104 is preferably made of a relatively soft plastic having a Shore A hardness of between about 40 and about 70. For purposes of shaping the distal section and its distal tip 106, the core 116 may be formed of a suitable metal wire or harder but flexible plastic that will retain a shape. The proximal section 102 may comprise a metal tube or rigid plastic since its flexibility and softness are not required.

In operation the operator rotates the tubular cylinder 114 counter clockwise to align the lugs 120 with channels 118' and, if required, advances the distal section 104 distally by contacting the tubular cylinder through the proximal port 112 with a finger or fingers of the hand grasping and supporting the introducer 100. With the lugs 120 in the channels 118" the distal section 104 will not rotate with respect to the proximal section 102 and cannot be over extended because the lugs will be stopped by the terminus of the channels. The introducer can be disassembled by fully retracting the distal section 104 and rotating the tubular cylinder counter clockwise until the corresponding lugs 120 contact the stops 124 that align the lugs with the channels 118'. The distal section 104 can then be fully withdrawn and separated from the proximal section 102 since the channels open to the mouth of the bore 108 and the lugs are free to move distally beyond the proximal section.

While the invention has thus far been described in connection with the manual advancement of the extendable member of the introducer it will be understood that it is within the scope of the invention to include components for mechanical or automated operation of the extendable member. For example a spring located in the proximal portion of the introducer is compressed when the extendable member is fully retracted. A latch activated by the operator's finger acting against a latch release causes the spring to urge the extendable member into an extended position. Likewise the spring can be released by a radio activated or infrared activated switch remotely located such as, for example, on a videoscope of laryngoscope being used for the intubation. In such cases advancement of the extendable member is accomplished without the necessity of the operator changing hand positions.

We claim:

1. An introducer for the introduction of an airway tube into the trachea of a patient, the introducer comprising:
a an elongated tubular body defining a bore, a proximal end and a proximal end portion and a distal end and a distal end portion, the elongated tubular body having an outside dimension less than an inside diameter of an airway tube for being received in a bore of the airway tube and for guiding the airway tube into the trachea of a patient after introduction of the elongated tubular body into the trachea of the patient;

b a flexible elongated guide member movably disposed in the bore of said elongated tubular body for rotation, extension and retraction of the flexible elongated guide member with respect to the distal end of said elongated tubular body; and c two ports in a wall of the elongated tubular body for communication with the bore of the elongated tubular body for manual contact with the flexible elongated guide member to maneuver the flexible elongated guide member disposed therein.

2. The introducer of claim 1 wherein the two ports are located on the elongated tubular body medially of the proximal end and the distal end.

3. The introducer of claim 2 wherein the two ports are located at a point adapted for an operator to place a hand to support the elongated tubular body during an intubation procedure whereby an operator can support the introducer and maneuver the flexible elongated guide member with one hand.

* * * * *